United States Patent [19]

Moll et al.

[11] Patent Number: 5,356,932

[45] Date of Patent: Oct. 18, 1994

[54] METHODS AND COMPOSITIONS FOR CONTROLLING INTRAOCULAR PRESSURE WITH TRANSITION METAL COMPLEXES

[75] Inventors: Hans R. Moll, Weatherford; Mark T. DuPriest, Fort Worth; Daniel Kuzmich, Lewisville, all of Tex.

[73] Assignee: Alcon Laboratories, Inc., Fort Worth, Tex.

[21] Appl. No.: 104,242

[22] Filed: Aug. 9, 1993

Related U.S. Application Data

[63] Continuation of Ser. No. 680,641, Apr. 2, 1991, abandoned, which is a continuation of Ser. No. 354,583, May 22, 1989, abandoned.

[51] Int. Cl.$^5$ .......................................... A61K 31/295
[52] U.S. Cl. .................................. 514/502; 514/492; 514/913
[58] Field of Search .................. 514/492, 502, 913

[56] References Cited

PUBLICATIONS

Chem Abst. 100: 201286e (1984). Herak et al.
Sawyer et al., *J. Amer. Chem. Soc.*, vol. 81, 816 (1959).
Britzinger et al., *Z. Anorg. Chem.*, vol. 251, 289 (1943) (ref. Beilstein, vol. 4, III, 1988).
Cohen et al., *J. Amer. Chem. Soc.*, vol. 88, 3228 (1966).
Belcher, R. et al., *Talanta*, 1959, 3, 201.
Nakashima, H.; Miyake, M., *Yakugaku*, 1972, 21 416.
Hertzberg, R. P.; Dervan, R. R., *Biochemistry*, 1984, 23, 3934.
Haner, M.; Eidson, A. F.; Darnall, D. W.; Birnbaum, E. R., *Arch. Biochem. Biophys.*, 1984, 231, 477.
Yeh, S. M.; Sherman, D. G.; Meares, C. F., *Anal. Biochem.*, 1979, 100, 152.
Swift, G.; Swern, D., *J. Org. Chem.*, 1967, 32, 511.
Martin, R. L.; Norcorss, B. E., *J. Org. Chem.*, 1975, 40, 523.
Feit, P. W.; Nielsen, O. T., *J. Med. Chem.*, 1967, 10, 927.
Kohn, H.; Jung, S-H., *J. Am. Chem. Soc.*, 1983, 103, 4106.
Becker, P. N.; Bergman, R. G. *Organomet.*, 1983, 2, 787.
Sawyer et al., *J. Amer. Chem. Soc.*, vol. 82, p. 4191, (1960).
Mather, J. D.; Tapscott, R. E., *J. Coord. Chem.*, 1981, 11(1), 5.10.

*Primary Examiner*—Zohreh Fay
*Attorney, Agent, or Firm*—Sally Yeager

[57] ABSTRACT

Compositions and methods for controlling intraocular pressure using transition metal complexes are disclosed. Topical ophthalmic and systemic administration of the transition metal complexes is disclosed.

12 Claims, No Drawings

METHODS AND COMPOSITIONS FOR CONTROLLING INTRAOCULAR PRESSURE WITH TRANSITION METAL COMPLEXES

This application is a continuation, of application Ser. No. 07/680,641 filed on Apr. 2, 1991, now abandoned which is a continuation of U.S. Ser. No. 07/354,583, filed May 22, 1989 now abandoned.

The present invention is directed to metal complexes which are useful in controlling ocular hypertension. In particular, the complexes are useful in controlling ocular hypertension associated with primary open angle glaucoma. The present invention is also directed to methods for controlling ocular hypertension by the administration of compositions comprising the metal complexes.

According to the present invention, it has been found that metal complexes, some of which are known and some of which are new, particularly transition metal complexes ("TMC") of the following general structure, lower and control intraocular pressure ("IOP"):

$$L_p M_m \qquad [A]$$

wherein L is an organic ligand, M is a transition metal ion and p and m are integers reflecting the nature of the complex, i.e., the ratio of L to M. Examples of preferred TMC are represented by the following structure:

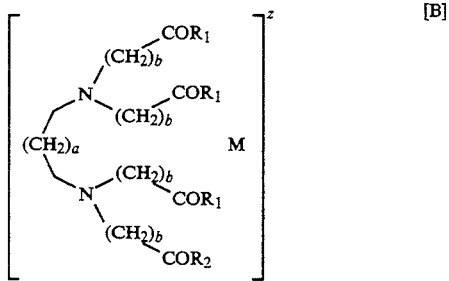

wherein:
a is 0 or 1;
b is 1 or 2;
m is $Fe^{+3}$, $Fe^{+2}$, $Co^{+3}$, $Cr^{+3}$, $V^{+3}$, $Cu^{+2}$ or $Mn^{+2}$
$R_1 = R_2 = $ —OH or —O—; or
$R_1 = $ —OH or —O— and $R_2 = $ —O-alkyl ($C_1$ through $C_{18}$), —O-aryl, —O-alkyl-aryl, —NH-$(CH_2)_n$—NH-peptide (or protein) wherein $n = 1$–6, or —$NR_3R_4$, wherein $R_3$ and/or $R_4$ can be hydrogen, any saturated or unsaturated alkyl or cycloalkyl group ($C_1$ through $C_{18}$), any aryl, alkylaryl, heteroalkyl and heteroaryl group with or without one or more functional groups such as F, Cl, Br or I; amino, imino or nitrilo; alcohol, ether, carbonyl or carboxyl including esters and amides; thiol, thioether, sulfoxide or sulfone; thiocarboxyl and sulfonate including esters and amides; and any phosphorous containing functional group. In addition one or more of any H-atom present in the four acid moieties and/or in the diamine moieties may be substituted by one or more of the following groups: straight chain and/or branched saturated and unsaturated alkyl groups up to 14 carbons; single and/or polynuclear aryl groups up to 14 carbons; alkyl-aryl groups up to 14 carbons; or saturated and/or unsaturated mono or polynuclear heterocyclic groups. Substitution can result in annelation, giving rise to cyclic and polycyclic molecules. These groups which can be substituted for one or more H atoms and which can give rise to cyclic and polycyclic molecules can contain one or more of the following functional groups, in particular: halogen, such as F, Cl Br or I; amino, imino or nitrilo functions; alcohol, ether, carbonyl and carboxyl functions, including esters and amides; thiol, thio ether, sulfoxide; sulfone, thiocarboxylic and sulfonic acid functions; and phosphorus containing functions. z is $-1$ when $R_1 = R_2 = $ —O— or OH and M is $Fe^{+3}$, $Co^{+3}$, $Cr^{+3}$ or $V^{+3}$; z is $-2$ when $R_1 = R_2 = $ —O— or —OH and M is $Fe^{+2}$, $Cr^{+2}$ and Z is or $Mn^{+2}$ and z is 0 when $R_1$ is —O— or —OH, $R_2$ is an ester or an amide and M is $Fe^{+3}$, $Co^{+3}$, $Cr^{+3}$, or $V^{+3}$.

The most preferred TMC are the iron ($Fe^{+3}$, $Fe^{+2}$) complexes of the organic ligands.

The TMC of the present invention as described above include all sterio-isomers of the TMC.

The TMC of the present invention are formed by reacting the organic ligands with metal ions which are capable of complexing substantially simultaneously with both the nitrogen atoms and the carboxylate groups of the organic ligands, resulting in anionic hexadentates or anionic or neutral tetra- and pentadentates as shown in [B]. The TMC will be anionic or uncharged depending on the oxidation level of the metal ion and the nature of the ligands. Typically the metal ions will be selected from the group consisting of $Fe^{+3}$, $Co^{+3}$, $Cr^{+3}$, $V^{+3}$, $Cu^{+2}$ and $Mn^{+2}$, preferably $Fe^{+3}$. The synthesis of such TMC is known to those skilled in the art. In general, stoichiometric amounts of the ligand of choice and a water soluble salt of a transition metal such as $FeCl_3$, $Fe(NO)_3$ or $CuCl_2$ are refluxed in water for 5 minutes to an hour. The pH is then adjusted to between 5 and 7 with an appropriate base to provide for the desired salt on crystallization. Most of the water is then evaporated and the TMC is recrystallized from an alcohol, such as methanol, ethanol, propanol, or alcohol/water mixtures. The formation of $Na^+$, $NH_4^+$ and $Ca^{+2}$ salts are described; see for example, Sawyer et al., J. Amer. Chem. Soc., Vol. 81,816 (1959); Britzinger et al., Z. Anorg. Chem., Vol. 251, 289 (1943) (ref. Beilstein, Vol. 4, III, 1988); and Cohen et al., J. Amer. Chem. Soc., Vol. 88, 3228 (1966).

Organic ligands which are reacted with metals to form TMC as described above can be made by several methods. In general, this is accomplished by tetraalkylation of the desired diamine with the appropriate acetate or propionate derivative. The diamino compounds are prepared using standard synthetic methodology familiar to those skilled in the art as described below.

Tetraacetic acid derivatives can be obtained by alkylation of the diamino compound with an excess of an ester of chloro or bromoacetate such as methyl, ethyl, or t-butyl, followed by ester hydrolysis under either acidic (e.g. trifluoroacetic acid or aqueous hydrochloric acid) or basic (e.g. excess sodium or potassium hydroxide or carbonate in aqueous alcohol) conditions. Tetraalkylation can be accomplished in a solvent such as t-butanol in the presence of a base such as sodium or potassium carbonate at 50° C. to reflux for 18 to 48 hours. An alternate method is to use an excess of chloro or bromoacetic acid (for example, see Belcher, R. et. al., Talanta 1959, 3, 201).

Tetrapropionic acid derivatives can be obtained by tetraalkylation using acrylonitrile under forcing conditions followed by hydrolysis of the nitrile functionalities to carboxylic acids using concentrated hydrochloric acid or aqueous sulfuric acid. Alternatively, dialkylation to provide N,N'-dipropionic acids is accomplished by alkylation under milder conditions followed by hydrolysis. In this way, N,N'-dipropionic-N,N'-diacetic acids can be obtained by alkylation of the intermediate diacid with an acetic acid derivative as described above.

N,N'-Diacetic acid-N,N'-di-α-substituted acetic acids can be prepared by initial dialkylation of the diamino compound with an α-halo carboxylic acid (other than a haloacetic acid) to obtain an N,N'-di-α-substituted acetic acid followed by dialkylation with chloro or bromoacetic acid or an ester thereof as described above. (For example, see Nakashima, H.; Miyake, M., *Yukagaku* 1972, 21,416).

N,N,N'-Triacetic acid-N'-acetate compounds can be obtained by incomplete hydrolysis of the tetraesters (for example, see Bellstein, Vol. 4, Series III, p.1187).

Monoamide derivatives of ethanediaminetetraacetic acids or propanediaminetetraacetic acids can be prepared by either of two different methods. In the first method, tetraethyl ester derivatives of the diaminetetraacetic acids are hydrolyzed to the triesters using one equivalent of sodium hydroxide in the presence of copper(II) perchlorate. Amide formation is then accomplished with the desired amine and 1,1'-carbonyldiimidazole. The remaining ester functionalities are then hydrolyzed using lithium hydroxide in ethanol (for example, see Hertzberg, R. P.; Dervan, P. B., *Biochemistry* 1984, 23, 3934). The second procedure involves the formation of the cobalt(III) complex of the diaminetetraacetic acid followed by formation of the amide derivative of the uncoordinated carboxylic acid functionality by using the desired amine and 1-ethyl-(3-dimethylaminopropyl) carbodiimide. The cobalt is then removed from the complex by reduction using iron(II) sulfate and ascorbate at pH 5 to provide the desired monoamide ligand (for example, see Haner, M.; Eidson, A. F.; Darnall, D. W.; Birnbaum, E. R., *Arch. Biochem. Biophys.* 1984, 231, 477).

Many methods are available for the preparation of substituted ethanediamines and propanediamines. Monosubstituted ethanediamines can be prepared from α-substituted amino acids by conversion of the carboxylic acid functionality to an amide followed by reduction of the amide to an amine (for example, see Yeh, S. M.; Sherman, D. G.; Meares, C. F., *Anal, Biochem.* 1979, 100, 152). Primary, vicinal diamines can be obtained from a large variety of substituted olefins using several different methods. Olefins can be oxidized to epoxides which are then reacted with azide to provide azide alcohols. Mesylation foil)owed by azide displacement provides a vicinal diazide which can be reduced to the diamine (for example, see Swift, G.; Swern, D., *J. Org. Chem.* 1967, 32, 511). Or olefins can be oxidized to vicinal diols which can be converted to vicinal diamines by the three step sequence consisting of dimesylation, displacement with azide, and azide reduction (for example, see Martin, R. L.; Norcross, B. E., *J. Org. Chem.* 1975, 40, 523 or Feit, P. W.; Nielsen, O. T., *J. Med. Chem.* 1967, 10, 927). Another multistep method is that of Kohn (Kohn, H.; Jung, S-H., *J. Am. Chem. Soc.* 1983, 103, 4106) which consists of reaction of the olefin with cyanamide and N-bromosuccinimide to provide an alkyl cyanamide that is treated with ethanolic hydrogen chloride to effect hydrolysis to an isourea that is cyclized to an imidazoline using triethylamine or sodium bicarbonate which is then hydrolyzed to the diamine using barium hydroxide. Another method is the reaction of olefins with cyclopentadienylnitrosylcobalt dimer in the presence of nitric oxide followed by reduction with lithium aluminum hydride (see Becker, P. N.; Bergman, R. G. *Organomet.* 1983, 2, 787).

1,3-Propanediamines with one or two substituents at the 2 position are available by initial alkylation of malonic acid diesters, reduction of the ester functionalities to alcohols using lithium aluminum hydride, conversion of the alcohols to mesylates, mesylate displacement with either azide or phthalimide, and, with azides, reduction or, with phthalimides, hydrolysis to the diamines. 1,3-Propanediamines substituted at the 1 and/or 3 positions can be obtained from the corresponding 1,3-dicarbonyl compound by conversion to the dioxime followed by reduction to the diamine. This general method is also applicable to 1,2,3-trisubstituted-1,3-propanediamines by starting with the appropriate 2-substituted-1,3-dicarbonyl compound.

Transition metal complexes of the present invention can be made as described herein. The following specific ligands can be reacted with transition metals to form TMC which are useful in lowering and controlling IOP.

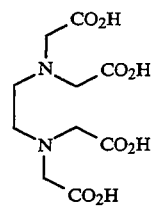

[1]

N,N'-(1,2-Ethanediyl)bis[N-(carboxymethyl)glycine]
(available from Sigma Chemical Co. as the iron complex

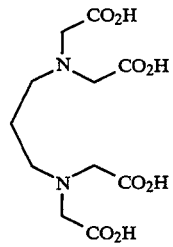

[2]

N,N'-(1,3-Propanediyl)bis[N-carboxymethyl)glycine]

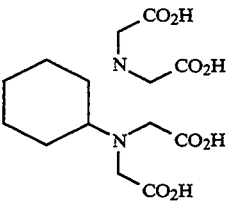

[3]

N,N'-(trans-1,2-Cyclohexanediyl)bis[N-(carboxymethyl)glycine]

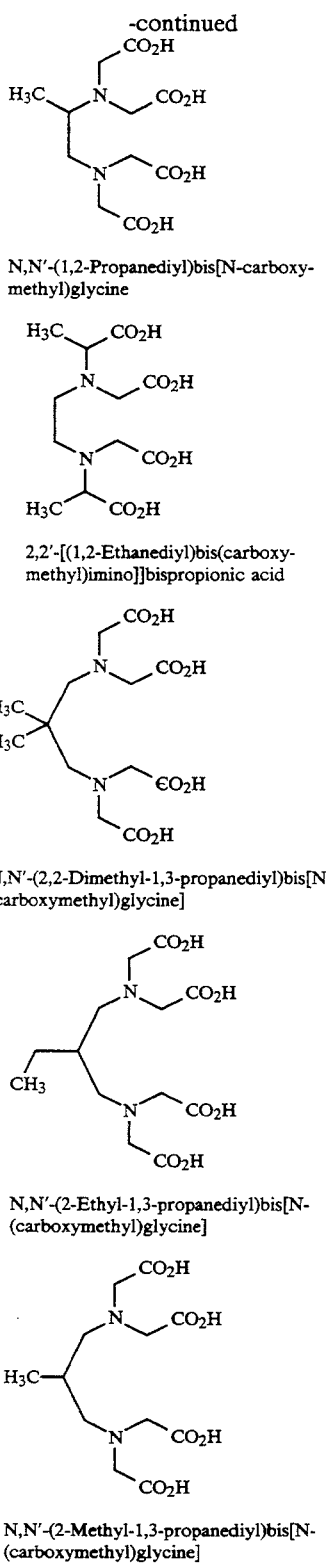

[4] N,N'-(1,2-Propanediyl)bis[N-carboxymethyl)glycine

[5] 2,2'-[(1,2-Ethanediyl)bis(carboxymethyl)imino]]bispropionic acid

[6] N,N'-(2,2-Dimethyl-1,3-propanediyl)bis[N-(carboxymethyl)glycine]

[7] N,N'-(2-Ethyl-1,3-propanediyl)bis[N-(carboxymethyl)glycine]

[8] N,N'-(2-Methyl-1,3-propanediyl)bis[N-(carboxymethyl)glycine]

Persons suffering from primary open angle glaucoma (POAG) experience a buildup of amorphous extracellular material in the eyes' trabecular meshwork. This buildup prevents the normal exit of aqueous humor from the anterior and posterior chambers of the eyes resulting in raised intraocular pressures. Such raised pressures translate into pressure on the optic nerve, which if untreated, over time can lead to blindness. Compositions comprising TMC can, according to the methods of this invention, be administered to lower and control the ocular hypertension associated with POAG.

The transition metal complexes of the present invention may be incorporated in various formulations for delivery to the eye. For example, topical formulations can be used and can include ophthalmologically acceptable preservatives, surfactants, viscosity enhancers, buffers, sodium chloride and water to form aqueous sterile ophthalmic solutions and suspension. In order to prepare sterile ophthalmic ointment formulations, a transition metal complex is combined with a preservative in an appropriate vehicle, such as mineral oil, liquid lanolin or white petrolatum. Sterile ophthalmic gel formulations comprising TMC can be prepared by suspending the TMC in a hydrophilic base prepared from a combination of, for example, Carbopol-940 (a carboxyvinyl polymer available from B.F. Goodrich Company) according to published formulations for analogous preparations. Preservatives and tonicity agents may also be incorporated in such gel formulations.

The TMC can also be administered systemically. For example, the compounds can be administered orally as incapsulated solids or as aqueous solutions. The compounds can also be administered intravenously or intraperitoneally as aqueous solutions.

The specific types of formulations selected will depend on various factors, such as the TMC being used and the dosage frequency. Topical ophthalmic aqueous solutions, suspensions and gels of TMC of ligands [1], [2], [3] and [4] are preferred dosage forms. Topical formulations of the $Fe^{+3}$ complex of ligand [4] is particularly preferred. The TMC will normally be contained in the formulation at a concentration between about 0.2 and 6.0 weight percent (wt. %), preferably 2.0 to 4.0 wt. %, most preferably about 2.0 wt. %. Thus for topical administration the formulations are delivered to the surface of the eye one to four times per day, depending on the routine discretion of the skilled clinician.

The present invention is also directed to methods for using the compounds of the present invention. The compounds in compositions, such as aqueous compositions described above, can be delivered topically to the eye, intraocularly, systemically, such as intravenously or orally for the prevention and/or control of ocular hypertension.

The following examples are illustrative of complexes and formulations comprising the complexes which can be used according to the present invention for the control of intraocular pressure.

EXAMPLE 1

Preparation of N,N'-(1,3-Propanediyl)bis[N-(carboxymethyl)glycine], iron complex, sodium salt The iron complex, sodium salt of ligand [2] was prepared from commercially available propylenediaminetetraacetic acid (Aldrich Chemical Company) using the general method described in Sawyer et al., J. Amer. Chem. Soc., Vol.82, p. 4191 (1960).

EXAMPLE 2

Preparation of N,N'-(trans-1,2-Cyclohexanediyl)bis[N-(carboxymethyl) glycine], iron complex, sodium salt The iron complex, sodium salt of ligand [3] was prepared from commercially available trans-1,2- diaminocyclohexane-N,N,N',N'-tetraacetic acid hydrate (Aldrich Chemical Company) as described below.

To a suspension of trans-1,2-diaminocyciohexane-N,N,N',N'-tetraacetic acid hydrate (10 g, 28.9 mmol) in 0.5M aqueous ferric chloride (57.8 ml, leq) was added portionwise sodium bicarbonate until the pH was 5.5. The mixture was refluxed for 20 rain, cooled, filtered through celite, and evaporated. The residue was taken up in warm (70° C.) dimethylsulfoxide (200 mL) and filtered to remove inorganic salts. After the dimethylsulfoxide was removed by evaporation, the residue was recrystallized from water/ethanol to provide 5.5 g (45%) of the complex as green crystals.

Anal. Calcd. for $C_{14}H_{18}N_2O_8FeNa \cdot 2H_2O$: C, 36.78; H, 4.85; N, 6.12 Found: C, 36.27; H, 4.90; N, 6.12.

EXAMPLE 3

Preparation of N,N'-(1.2-Propanediyl)bis[N-(carboxymethyl) glycine], iron complex, sodium salt The iron complex, sodium salt of ligand [4] was prepared from commercially available 1,2-diaminopropane-N,N,N',N'-tetraacetic acid (Aldrich Chemical Company) as described below.

1,2-Diaminopropane-N,N,N', N'-tetraacetic acid (10.0 g, 32.6 mmol) was treated with leq of 0.5M aqueous ferric chloride as described in Example 2. Recrystallization from water/ethanol provided 11.2 g (90%) of the complex as a yellow solid.

Anal. Calcd. for $C_{11}H_{14}N_2O_8FeNa \cdot 1.5H_2O$: C, 32.37; H, 4.20; N, 6.86. Found: C, 32.17; H, 4.26; N, 6.78.

EXAMPLE 4

Preparation of 2,2'-[(1,2-Ethanediyl)bis[(carboxymethyl)-iminol] bisproptonic acid, iron complex, sodium salt The iron complex, sodium salt of ligand [5] was prepared from commercially available ethylenediamine-N,N'-diacetic acid-N,N'-di-α-propionic acid (Sigma Chemical Company) as described below.

Ethylenediamine-N,N'-diacetic acid-N,N'-di-α-propionic acid (5.0 g, 15.6 mmol) was treated with leq of 0.5M aqueous ferric chloride as described in Example 2. Recrystallization from water/ethanol provided 1.2 g (19%) of the complex as a bright yellow solid.

Anal. Calcd. for $C_{12}H_{16}N_2O_8FeNa \cdot 2H_2O$: C, 33.43; H, 4.66; N, 6.50. Found: C, 33.58; H, 4.63; N, 6.47.

EXAMPLE 5

Preparation of N,N'-(2-Ethyl-1,3-propanediyl)bis[N-carboxymethyl)glycine], iron complex, sodium salt The synthesis of 2-ethyl-1,3-propanediamine-N,N,N',N'-tetraacetic acid and formation of the iron complex are described below.

Under nitrogen, a solution diethyl ethylmalonate (88 g, 0.47 mol) in anhydrous tetrahydrofuran (THF) (300 mL) was added over 30 min to a 0° C. suspension of lithium aluminum hydride (LAH) in tetrahydrofuran (300 mL). The reaction was stirred at room temperature overnight and then refluxed for 6 h. The mixture was cooled to 0° C. and the excess LAH was cautiously quenched with water. Magnesium sulfate was added and the mixture was filtered through celite, washing with THF/methylene chloride. Solvent evaporation left 15 g of crude product as a clear oil. Additional material was obtained by washing the filter cake with acetone/methanol. The crude material was distilled to provide 30 g (61%) of 2-ethyl-1,3-propanediol; bp 90°-94° C./0.2 mm.

Under nitrogen, triethylamine (166 mL, 0.48 mol, 2 eq) was added to a 0° C. mixture of 2-ethyl-1,3-propanediol (30 g, 0.29 mol) and methanesulfonyl chloride (0.48 mol, 88 mL, 2 eq) over 45 min. The mixture was warmed to room temperature, stirred overnight, and then filtered, washing with ethyl acetate. The filtrate was evaporated and the residue was diluted with water (300 mL) and extracted with ethyl acetate. The combined organic layers were washed with brine, dried over $MgSO_4$, treated with decolorizing carbon, filtered through celite, and concentrated to provide 72 g of crude product. This was passed through a pad of silica gel using a gradient of 10% ethyl acetate in hexane to pure ethyl acetate to provide, after solvent removal, 62 g (82%) of 2-ethyl-1,3-propanediol dimesylate as an oil.

A mixture of 2-ethyl-1,3-propanediol dimesylate (60 g, 0.23 mol) and potassium phthalimide (94 g, 2.2 eq) in dimethylformamide (700 mL) was heated at 70° C. for)5 h. The reaction was then poured into ice water (3 L) and filtered, washing with water. The still moist solid was dissolved in refluxing ethyl acetate (1.5 L) and the solution was treated with decolorizing carbon, dried over $MgSO_4$, filtered, and concentrated to about 250 mL at which point the solid was collected by filtration, washing with diethyl ether, to provide 53 g (63%) of 1,3-diphthalimido-2-ethylpropane as a white solid.

A mixture consisting of 1,3-diphthalimido-2-ethylpropane (25 g, 69 mmol) concentrated hydrochloric acid (700 mL), and ethanol (700 mL) was refluxed for 6 days with additional concentrated hydrochloric acid being added at the indicated time; 3 days (300 mL), 4 days (200 mL), 5 days (200 mL). The reaction was evaporated to dryness and the residue was diluted with water (200 mL), chilled, and filtered. The filtrate was washed with ethyl acetate (5×500 mL) and evaporated to leave 12 g (100%) of 2-ethyl-1,3-propanediamine dihydrochloride as a thick oil.

A mixture of 2-ethyl-1,3-propanediamine dihydrochloride (10 g, 57.4 mmol), potassium carbonate (63 g, 0.46 mol, 8 eq), t-butyl chloroacetate (51 g, 0.34 mol, 6 eq), t-butanol (75 mL), and water (10 mL) was refluxed for 24 h. The mixture was then cooled, diluted with water (500 mL), and extracted with ethyl acetate. The combined organics were washed with brine, dried over $MgSO_4$, and evaporated to provide 27.6 grams of crude product. This was passed through a pad of silica gel using 10% ethyl acetate in hexane to provide 24.4 g (76%) of 2-ethyl-1,3-propanediamine-N,N,N',N'-tetraacetic acid tetra-t-butyl ester as a clear oil.

A mixture of 2-ethyl-1,3-propanediamine-N,N,N',N'-tetraacetic acid tetra-t-butyl ester (23.3 g, 41.7 mmol) and 6N aqueous hydrochloric acid (500 mL) was stirred at room temperature for 18 h. The reaction was then evaporated to dryness to provide 18.9 g (100%) of 2-ethyl-1,3-propanediamine-N,N,N',N'-tetraacetic acid dihydrochloride as a white hygroscopic solid.

2-Ethyl-1,3-propanediamine-N,N,n',N'tetraacetic acid dihydrochloride (10.0 g, 24.6 mmol) was dissolved in distilled water (20 mL) and 0.5M aqueous ferric chloride (40 mL, 0.81 eq) was added. The pH was adjusted to 5.1 by adding sodium bicarbonate portionwise and the mixture was refluxed for 15 min, cooled, filtered through celite, and evaporated. The residue was taken up in warm (70° C.) dimethylsulfoxide (150 mL) and filtered to remove inorganic salts. The viscous oil that remained after the dimethylsulfoxide was removed by evaporation could not be crystallized, so the material was resubjected to 15 mL of 0.5M aqueous ferric chloride at pH 5.4 at reflux for 20 min. The ;mixture was filtered through celite and the filtrate was adjusted to pH 5.1 and evaporated. The residue was taken up in methanol, filtered, and concentrated. Recrystallization from methanol provided 5 g (50%) of N,N'-(2-ethyl-1,3 propanediyl) bis[N-(carboxymethyl)glycine], iron complex sodium salt as a yellow solid.

Anal. Calcd. for $C_{13}H_{18}N_2O_8FeNa$: C, 38.16; H, 4.43; N:, 6.85; Na, 5.62. Found: C, 38.05; H, 4.39; N, 6.84; Na, 5.27.

EXAMPLE 6

Preparation of
N,N'-(2-Methyl-1,3-propanediyl)bis[N-(carboxymethyl)glycine], iron complex, sodium salt The synthesis of 2-methyl-1,3-propanediamine-N,N,N',N'-tetraacetic acid and formation of the iron complex are described below.

1,3-Diphthalimido-2-methylpropane was prepared form commercially available 1-bromo-2-chloro-2-methylpropane (Aldrich Chemical Company) using the method described in Mather, J. D.; Tapscott, R. E., *J. Coord. Chem.* 1981, 11(1), 5.10.

1,3-Diphthalimido-2-methylpropane (32 g, 91.9 mmol) was hydrolyzed using the method described for the preparation of 2-ethyl-1,3-propanediamine dihydrochloride in Example 5 to provide 7.1 g (50%) of 2-methyl-1,3-propanediamine dihydrochloride.

2-Methyl-1,3-propanediamine dihydrochloride (7.1 g, 44.3 mmol) was tetraalkylated using the method described for the preparation of 2-ethyl-1,3-propanediamine-N,N,N',N'-tetraacetic acid tetra-t-butyl ester in Example 5 to provide 15.6 g (65%) of 2-methyl-1,3-propanediamine-N,N,N',N'-tetraacetic acid tetra-t-butyl ester.

2-Methyl-1,3-propanediamine-N,N,N',N'-tetraacetic acid tetra-t-butyl ester (15 g, 27.5 mmol) was hydrolyzed using the method described for the preparation of 2-ethyl-1,3-propanediamine-N,N,N',N'-tetraacetic acid dihydrochloride in Example 5 to provide 11.4 g (94%) of 2-methyl-1,3-propane-diamine-N,N,N', N'-tetraacetic acid dihydrochloride.

2-Methyl-1,3-propanediamine-N N,N',N'-tetraacetic acid dihydrochloride (11.0 g, 28.0 mmol) was treated with 0.5M ferric chloride using the method described for the preparation of N,N'-(2-ethyl-1,3-propanediyl)-bis[N-(carboxymethyl)glycine], iron complex, sodium salt in Example 5 to provide 8.8 g (83%) of N,N'-(2-methyl-1,3-propanediyl)bis]N-(carboxymethyl)glycine], iron complex sodium salt.

Anal. Calcd. for $C_{12}H_{17}N_2O_8FeNa$: C, 36.27; H, 4.08; N, 7.09; Na, 5.80. Found: C, 36.76; H, 3.95; N, 7.07; Na, 5.29.

EXAMPLE 7

Preparation of
N,N'-(2,2-Dimethyl-1,3-propanediyl)bis[N-(carboxymethyl)glycine], iron complex, sodium salt The preparation of 2,2-dimethyl-1,3-propanediamine-N,N,N',N'-tetraacetic acid from commercially available 2,2-dimethyl-1,3-propanediamine (Aldrich Chemical Company) and formation of the iron complex are described below.

2,2-Dimethyl-1,3-propanediamine (2.8 g, 27 mmol) was tetraalkylated using the method described for the preparation of 2-ethyl-1,3-propanediamine-N N,N',N'-tetraacetic acid tetra-t-butyl ester in Example 5 to provide 12.2 g (80%) of 2,2-dimethyl-1,3-propanediamine-N,N,N',N'-tetraacetic acid tetra-t-butyl ester.

2,2-Dimethyl-1,3-propanediamine-N,N,N',N'-tetraacetic acid tetra-t-butyl ester (62 g, 0.11 mol) was hydrolyzed using the method described for the preparation of 2-ethyl-1,3-propanediamine-N,N,N',N'-tetraacetic acid dihydrochloride in Example 5 to provide 36.6 g (87%) of 2,2-dimethyl-1,3-propanediamine-N,N,N',N'-tetraacetic acid dihydrochloride.

2,2-Dimethyl-1,3-propanediamine-N,N,N',N'-tetraacetic acid dihydrochloride (5.0 g, 12.2 mmol) was treated with 0.5M ferric chloride using the method described for the preparation of N,N'-(2-ethyl-1,3-propanediyl)bis[N-(carboxymethyl)glycine], iron complex, sodium salt in Example 5 to provide 3.4 g (68%) of N,N'-(2,2-dimethyl-1,3-propanediyl)bis[N-(carboxymethyl)glycine], iron complex, sodium salt (recrystallized from ethanol/water).

Anal. Calcd. for $C_{13}H_{18}N_2O_8FeNa$: C, 38.16; H, 4.43; N, 6.85. Found: C, 38.27; H, 4.62; N, 6.79.

EXAMPLE 8

The following aqueous formulation can be applied topically to the eye to lower intraocular pressure.

| Ingredient | Concentration (w/v %) |
| --- | --- |
| N,N'-(1,2-Propanediyl)bis[N-(carboxymethyl) glycine], iron complex, sodium salt (Ligand 4 complex) | 2.04 |
| Mannitol | 3.6 |
| Purified water | q.s. to 100 ml |

Procedure

Approximately 85% (8.5ml) of the batch volume of purified water was added to a container. 204 mg of Ligand 4 complex and 360 mg of mannitol were added to the container and mixed well. The pH was adjusted to 6.0 with 0.01N NaOH. The solution was then filtered through a sterilizing filter into a sterile receiving vessel. Purified water (q.s. to 10 ml) was poured through the sterilizing filter and the solution was mixed well.

EXAMPLE 9

The following gel formulation can be applied topically to the eye to lower intraocular pressure.

| Ingredient | Concentration (w/v %) |
| --- | --- |
| Carbopol-940 (B. F. Goodrich Company) | 3.0 |
| Mannitol | 3.6 |
| Benzalkonium chloride (BAC) | 0.01 |
| N,N'-(1,2 Ethanediyl)bis[N-(carboxymethyl) glycine] iron complex, sodium salt (Ligand 1 Complex) | 2.0 |
| Purified water | q.s. to 100% |

Procedure

Place approximately 85% (8.5 ml) of the batch volume of purified water in a container. Add all of the ingredients to the container: 0.36 g mannitol; 0.2 g Ligand 1 complex;i 0.1 ml of 1% BAC; and 0.3 g carbopol and mix well. The pH is adjusted to 6.5 with 0.01N NaOH. Purified water (q.s. to 10 ml) is then added and mixed well to form a gel.

EXAMPLE 10

The following tablet formulation can be administered orally, one tablet, 1 to 4 times daily, for the control of intraocular pressure.

| Ingredient | Mg per tablet |
|---|---|
| Ligand 1 Complex | 200 mg |
| Starch | 150 mg |

Procedure

Combine Ligand 1 complex (200 mg) and the starch (150 mg) and mix in a P-K twin shell blender (Patterson-Kelly) for 10 minutes. Compress the blended material to form slugs using 1 inch flat face punches. The slugs can then be granulated by passing them through a 16 mesh-screen in a Stokes oscillating granulator (Penwalt Corp., Oak Brook, Ill.). The granulation is then transferred to a Colton rotary tablet press machine hopper (Vector Corp., Marion, Iowa) and compressed into tablets.

We claim:

1. A method for controlling intraocular pressure in persons suffering from primary open angle glaucoma which comprises, administering a composition comprising a therapeutically effective amount of a transition metal complex comprising an organic liquid which is a non-hetero compound of the following structure:

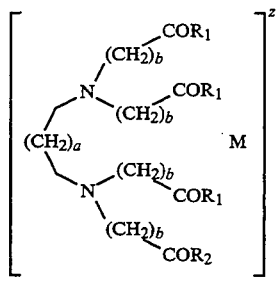

wherein:
a is 0 or 1;
b is 1 or 2;
M is a transition metal [$Fe^{+3}$, $Fe+2$, $Co^{+3}$, $Cr^{+3}$, $V^{+3}$, $Cu^{+2}$ or $Mn^{+2}$]; and
$R_1=R_2=$—OH or —O—; or
$R_1=$—OH or —O— and $R_2=$—O-alkyl, ($C_1$ through $C_{18}$), —O-aryl, —alkyl-aryl, —NH-$(CH_2)_n$-NH-peptide or protein, wherein n=1-6, or —$NR_3R_4$, wherein $R_3$ and/or $R_4$ can be hydrogen, any saturated or unsaturated alkyl or cycloalkyl group ($C_1$ through $C_{18}$), any aryl, alkylaryl, heteroalkyl and heteroaryl group with or without one or more functional groups such as F, Cl, Br or I; amino, imino or nitrilo; alcohol, ether, carbonyl or carboxyl including esters and amides; thiol, thioether, sulfoxide or sulfone; thiocarboxyl and sulfonate including esters and amides; and any phosphorous containing functional group; and one or more of any H-atom present in the four acid-moieties and-/or in the diamine moiety may be substituted by one or more of the following groups: straight chain and/or branched saturated and unsaturated alkyl groups up to 14 carbons; single and/or polynuclear aryl groups up to 14 carbons; alkyl-aryl groups up to 14 carbons; and z is −1 when $R_1=R_2=$—O— or OH and M is $Fe^{+3}$, $Co^{+3}$, $Cr^{+3}$ or $V^{+3}$; z is −2 when $R_1=R_2=$—O— or —OH and M is $Fe^{+2}$, $Cr^{+2}$ or $Mn^{+2}$; is 0 when $R_1$ is —O— or —OH, —$R_2$ is an ester or amide and M is $Fe^{+3}$, $Co^{+3}$, $Cr^{+3}$ or $V^{+3}$.

2. The method of claim 1 wherein M is selected from the group consisting of $Fe^{+3}$, $Fe^{+2}$, $Co^{+3}$, $Cr^{+3}$, $V^{+3}$, $Cu^{+3}$, or $Mn^{+2}$.

3. The method of claim 2 wherein M comprises $Fe^{+3}$.

4. The method of claim 1 wherein the concentration of the compound is about 0.2 to 6.0 weight percent.

5. The method of claim 4 wherein the concentration is between about 2.0 and 4.0 weight percent.

6. The method of claim 1 wherein the compound is selected from the group consisting of N,N'-(1,2-ethanediyl)bis[N-carboxymethyl)glycine], iron complex, sodium salt; N,N'-(1,3-propanediyl)bis-[N-(carboxymethyl)glycine] iron complex, sodium salt; N,N'-(trans-b 1,2-cyclohexanediyl)bis[N-(carboxymethyl) glycine], iron complex, sodium salt; N,N'-(1,2-propanediyl)bis[N-(carboxymethyl)glycine], iron complex, sodium salt; 2,2'-[(1,2-ethanediyl)bis[(carboxymethyl)imino]]bispropionic acid, iron complex, sodium salt; N,N'-(2,2-dimethyl-1,3-propanediyl)bis[N-(carboxymethyl)glycine, iron complex, sodium salt; N,N'-(2-ethyl-1,3-propanediyl)bis[N-(carboxymethyl)glycine], iron complex, sodium salt; and N,N'-(2-methyl-1,3-propanediyl)bis[N-(carboxymethyl)glycine], iron complex, sodium Salt.

7. The method of claim 6 wherein the compound comprises N,N'-(1,2-propanediyl )bis[N-(carboxymethyl)glycine] iron complex sodium salt.

8. The method of claim 6 wherein the compound concentration is between about 0.2 and 6.0 weight percent.

9. A method for controlling intraocular pressure in persons suffering from primary open angle glaucoma, which comprises administering topically to the eye a composition comprising a therapeutically effective amount of a compound selected from the group consisting of N,N'-(1,2-ethanediyl)bis[N-(carboxymethyl)glycine], iron complex, sodium salt; N,N'-(1,3-propanediyl)bis-[N-(carboxymethyl)glycine] iron complex, sodium salt; N,N'-(trans-1,2-cyclohexanediyl)-bis[N-(carboxymethyl) glycine], iron complex, sodium salt; N,N'-(1,2-propanediyl)bis[N-(carboxymethyl)glycine], iron complex, sodium salt; 2,2'-[(1,2-ethanediyl)-bis[(carboxymethyl)imino]]bispropionic acid, iron complex, sodium salt; N,N'-(2,2-dimethyl-1,3-propanediyl) bis[N-(carboxymethyl)glycine, iron complex, sodium salt; N,N'-(2-ethyl-1,3-propanediyl)bis[N-(carboxymethyl)glycine], iron complex, sodium salt; and N,N'-(2-methyl-1,3-propanediyl)bis[N-(carboxymethyl)glycine], iron complex, sodium salt.

10. The method of claim 9 wherein the compound comprises N,N'-(1,2-propanediyl )bis[N-(carboxymethyl)glycine] iron complex sodium salt.

11. The method of claim 9 wherein compound concentration is between about 0.2 and 6.0 weight percent.

12. The method of claim 11 wherein the concentration is between about 2.0 and 4.0 weight percent.

* * * * *